(12) United States Patent
Protopapa et al.

(10) Patent No.: US 6,203,791 B1
(45) Date of Patent: Mar. 20, 2001

(54) LECITHIN-BASED MICROEMULSIONS CONTAINING PROTEOLYTIC ENZYMES AND METHOD FOR PERMANENT ENZYMIC DEPILATION

(76) Inventors: Evangelia Protopapa, 6, Agrafon Street, Anixis GR-145 65; Aristotelis Xenakis, 48, Nikomidias Street, Nea Spyrmi Attikis GR-171 24; Spyridon Avramiotis, 137, Spartis Street, Kalithea Attikis GR-176 75; Konstantinos Sekeris, 9, Ithakis Street, Athens GR-112 57, all of (GR)

( * ) Notice: Subject to any disclaimer, the term of this patent is extended or adjusted under 35 U.S.C. 154(b) by 0 days.

(21) Appl. No.: 09/180,904
(22) PCT Filed: May 19, 1997
(86) PCT No.: PCT/GR97/00015
§ 371 Date: Apr. 26, 1999
§ 102(e) Date: Apr. 26, 1999
(87) PCT Pub. No.: WO97/44005
PCT Pub. Date: Nov. 27, 1997

(30) Foreign Application Priority Data

May 22, 1996 (GR) .............................................. 960100168

(51) Int. Cl.⁷ .............................. A61K 38/48; C14C 1/00
(52) U.S. Cl. .................................... 424/94.64; 424/93.63; 435/265
(58) Field of Search ................ 435/265; 424/94.64, 424/94.63

(56) References Cited

U.S. PATENT DOCUMENTS 5,716,639 * 2/1998 Carlsson et al. ..................... 424/450
6,004,580 * 12/1999 Backlund et al. ................... 424/450

FOREIGN PATENT DOCUMENTS 0 622 069 * 11/1994 (EP) .

OTHER PUBLICATIONS

Protopapa et al. Epitheor. Klin. Farmakol. Farmakokinet., Int. Ed. 1994, 8(2), pp. 84–88.*
Papadimitriou et al. Colloids Surf., B. 1993, 1(5), pp. 295–303.*

* cited by examiner

Primary Examiner—Jon P. Weber
Assistant Examiner—Vera Afremova
(74) Attorney, Agent, or Firm—Watov & Kipnes, P.C.

(57) ABSTRACT

The invention refers to depilatory preparations containing: proteolytic enzymes solubilized in microemulsions, formed with lecithin, aliphatic hydrocarbon, alipathic alcohol and buffer solution pH 7 to 9, value corresponding to the pH range near the optimum pH value for the catalytic activity of the proteolytic enzymes, to be applied for permanent enzymic depilation. The application of these preparations will assure, as shown by our experimental studies, more permanent depilation than the one resulting from other depilatory methods. The application of these preparations is suitable for every type of skin (fatty-resistant or dry-sensitive). The present invention introduces the use of microemulsions as a medium for the facilitated penetration of the enzymic activity in the epithelial cells of the skin, as shown by our studies.

20 Claims, No Drawings

LECITHIN-BASED MICROEMULSIONS CONTAINING PROTEOLYTIC ENZYMES AND METHOD FOR PERMANENT ENZYMIC DEPILATION

Lecithin-based microemulsions containing proteolytic enzymes and method for permanent enzymic depilation The present invention refers to the depilatory preparations of lecithin-based microemulsions containing proteolytic enzymes. The proposed invention introduces for the first time the use of microemulsions as media for the soubilization of proteolytic enzymic systems, that assist the penetration of active molecules through the phospholipidic membranes. In addition, the present invention refers to a depilation method, that applies the preparations of microemulsion containing the enzyme α-chymotrypsin, or the enzyme trypsin, for the depilation of any type of skin, as well as to the depilation method based on the sequential application of the preparation of microemulsion containing the enzyme α-chymotrypsin, followed by the application of the preparation of microemulsion containing the enzyme trypsin, depending on the particularities of each type of skin. The application of the depilatory preparations of microemulsions containing either the enzyme α-chymotrypsin, or the enzyme trypsin, or the sequential application first of the preparation of microemulsion containing the enzyme α-chymotrypsin, followed by the application of the preparation of microemulsion containing the enzyme trypsin, is carried out by simple spreading at appropriate intervals.

Experimental studies published by us for the first time in the international literature, have shown that the action of the enzyme α-chymotrypsin provokes destruction of the stem cells and of the hair follicle, explaining the positive results in depilation. Similar positive results in hair depilation also has trypsin, but with a milder action.

Microemulsions are systems consisting of a continuous inert organic medium, where water droplets are dispersed with the help of lecithin acting as a natural surfactant. The dispersion of the aqueous phase, where the enzyme molecules α-chymotrypsin or trypsin are located, is achieved by simple and gentle shaking.

Our invention improves the depilatory action of the enzymes α-chymotrypsin and trypsin, because of the fact that they are applied through the microemulsion. The shape of the microemulsion is such that allows its easy spreading over the whole surface of the skin to be depilated. Furthermore, the presence of the microemulsion offers the facility to be applied on every type of skin, such as the sensitive-dry ones, or the resistant-fatty ones.

We have also observed that the sequential application first of the preparation of microemulsion containing the enzyme α-chymotrypsin, followed by the application of the preparation of microemulsion containing the enzyme trypsin, provokes important degradation of the hair follicle, and that the sequential application first of the preparation of microemulsion containing, the enzyme α-chymotrypsin and then of the preparation of microemulsion containing the enzyme trypsin has better depilatory results than the sequential application first of the preparation of microemulsion containing the enzyme trypsin followed by the application of the one containing the enzyme α-chymotrypsin. We have also observed that the sequential application first of the preparation of microemulsion containing α-chymotrypsin followed by the application of the preparation of microemulsion containing trypsin, has much better depilatory results than the application of only one of each depilatory preparation of microemulsion containing either enzyme. In addition, we have observed that the sequential application of the preparation of microemulsion containing α-chymotrypsin followed by the application of the preparation of microemulsion containing trypsin, even at low concentrations of 0.05 mg/ml, had a degrading effect on the hair follicle, rendering thus, the preparations with low enzyme concentrations appropriate to be applied on dry, sensitive areas of the skin. On the other hand we have observed that the use of high enzyme concentrations on dry-sensitive skins, leads to a significant depilation but with an intense irritation. Therefore it is recommended to apply on such type of skins preparations with low enzyme concentrations. Moreover, the use of microemulsions as a carrier for the transdermal transfer of active macromolecules, such as the proposed enzymes, offers a considerable improvement of the enzyme depilation methodology, since the lecithin of the microemulsion interferes with the phospholipidic membrane of the epithelial cells, allowing the penetration of the enzymes in the cells.

The proposed proteolytic enzymes α-chymotrypsin and trypsin will be used in absolutely pure state. The enzymes will be stored lyophilized in a freezer ($-18°$ C.) so that they are kept constant, avoiding denaturation. For the production of the preparations the enzymes will be dissolved in a solution of hydrochloric acid 0.001 M in doubly distilled water (pH 3) obtaining concentrations of 1 to 5 mg/ml, and will be kept in a sterile environment in a freezer ($-18°$ C.). By this procedure the enzyme activity is kept unvaried for at least 8 months.

In parallel, lecithin-based microemulsions will be prepared according to the following: For every ml of final solution, 0.75 to 1 ml of aliphatic hydrocarbon are mixed with 20 to 75 mg of lecithin, 0 to 0.25 ml of aliphatic alcohol and 0.005 to 0.05 ml of buffer solution, pH 7 to 9. By mixing the above components, after gentle shaking, a clear solution (microemulsion) is obtained. This solution is thermodynamically stable and has, thus, unlimited time life. To avoid perturbing the stability by a possible partial evaporation of the organic constituents and consequently altering the total microemulsion composition, the solution is stored in cupped vessels.

The choice of the buffer solutions used for the preparations of microemulsions containing the proteolytic enzymes α-chymotrypsin or trypsin, is based on the optimum pH value for the activities of the above enzymes, which are 7.8 and 8.8 respectively. One possible buffer solution to use for the preparation of the lecithin-based microemulsions, is the solution of 0.1 M tris-hydroxymethylamino-methane-hydrochloric acid, for the pH range 7.5–9, although many other buffers, covering the desired range of pH values, can be used.

Just before applying the preparations the enzyme solution will be mixed with the lecithin-based microemulsion for the preparation of the final product, which, if stored at a temperature of about 2–6° C., retains its depilative action for at least three days.

According to a suggested materialization of the present invention, in sterilized vials of 2.5 ml will be placed 2 ml of lecithin-based microemulsion in isooctane, prepared by mixing 1.8 ml isooctane, 64 mg soy bean lecithin, 0.2 ml 1-propanol and, either 0.03 ml buffer solution 0.1 M tris-hydroxymethylamino-methane-hydrochloric acid, pH 7.5–8 for the preparations of α-chymotrypsin, or 0.03 ml buffer solution 0.1 M tris-hydroxymethylamino-methane-hydrochloric acid, pH 8.5–9 for the preparations of trypsin. In small sterilized capsules located in the vials and incorporated in a special cap, will be placed 0.03 ml of the solution containing, either the enzyme α-chymotrypsin, or the enzyme trypsin at a concentration of 3.4 mg/ml. The microemulsion containing vials, and the small capsules will be stored at a temperature of about 2–6° C. Before using the preparations and before opening the vial, by slightly pressing the cap, the capsule will be broken and the contained enzymic solution will be mixed with the microemulsion contained in the vial. By repeatedly shaking the vial, the final microemulsion will be prepared containing the enzyme α-chymotrypsin or the enzyme trypsin at a final concentration of 0.05 mg/ml, ready to be used. Alternatively to the small capsule, the enzymic solution may be kept in a separate vial and mixed in a similar way with the microemulsion solution just before use. The application of the final preparations on the skin to be depilated will be carried out immediately after and for three consecutive days. During this interval the preparations will be stored in a freezer (−18° C.).

By this way we finally offer for use:
a) Preparations of lecithin-based microemulsions containing the enzyme α-chymotrypsin at a concentration of 0.05 mg/ml and pH 7.5–8, and according to a proposed application of the invention at pH 7.8.
b) Preparations of lecithin-based microemulsions containing the enzyme trypsin at a concentration of 0.05 mg/ml and pH 8.5–9, and according to a proposed application of the invention at pH 8.8.

For areas of fatty resistant skins it is proposed to apply sequentially first the preparation of microemulsion containing the enzyme α-chymotrypsin and then the preparation of microemulsion containing the enzyme trypsin, whereas at areas of dry sensitive skins it is proposed to apply the preparations containing trypsin. It is up to the judgement of the specialist to propose the use of the preparations of microemulsion containing either α-chymotrypsin or trypsin for sequential applications, to increase the total quantity of either enzyme, depending on the type of skin.

What is claimed is:

1. A two part depilatory kit comprising first and second components which when combined together can effectively be spread on the skin to initiate depilatory activity, wherein comprises the following ratio of ingredients:
   40 to 150 mg of a lecithin;
   1.5 to 2 ml of an aliphatic hydrocarbon;
   optionally up to 0.5 ml of an aliphatic alcohol; and
   an amount of a buffer solution sufficient to provide a pH of 7 to 9,
the second component comprises the following ratio of ingredients:
   water; and
   a proteolytic enzyme in an amount sufficient to provide a proteolytic enzyme concentration of the second component of from 1 to 5 mg/ml,
and wherein the proteolytic enzyme concentration of the combination of the first and second components is from 0.01 to 0.1 mg/ml in a microemulsion.

2. The two part depilatory kit of claim 1 wherein the aliphatic hydrocarbon is isooctane.

3. The two part depilatory kit of claim 1 wherein the amount of the buffer solution is 0.01 to 0.1 ml.

4. The two part depilatory kit of claim 1 wherein the aliphatic alcohol is propanol-1.

5. The two part depilatory kit of claim 1 wherein the proteolytic enzyme is selected from the group consisting of α-chymotrypsin and trypsin.

6. The two part depilatory kit of claim 1 wherein the second component further comprises an effective amount 0.001M hydrochloric acid.

7. The two part depilatory kit of claim 1 wherein the amount of the proteolytic enzyme in the second component is sufficient to provide a concentration of the proteolytic enzyme in the second component of about 3.4 mg/ml and a concentration of the proteolytic enzyme in the composition of about 0.05 mg/ml.

8. The two part depilatory kit of claim 1 wherein the first component comprises:
   64 mg of a lecithin;
   1.8 ml of isooctane;
   0.2 ml of 1-propanol; and
   0.03 ml of a buffer providing a pH for said first component of 7.5 to 8.0; and
the second component comprises:
   0.03 ml of water containing α-chymotrypsin at a concentration of 3.4 mg/ml.

9. The two part depilatory kit of claim 1 wherein the first component comprises:
   64 mg of a lecithin;
   1.8 ml of isooctane;
   0.2 ml of 1-propanol;
   0.03 ml of a buffer providing a pH of said first component of 8.5 to 9.0; and
the second component comprises:
   0.03 ml of water containing trypsin at a concentration of 3.4 mg/ml.

10. A depilatory composition comprising a mixture of the two component of the kit of claim 1.

11. The depilatory composition of claim 10 wherein the aliphatic hydrocarbon compound is isooctane.

12. The depilatory composition of claim 10 wherein the amount of the buffer solution is 0.01 to 0.1 ml.

13. The depilatory composition of claim 10 wherein the aliphatic alcohol is 1-propanol.

14. The depilatory composition of claim 10 wherein the proteolytic enzyme is selected from the group consisting of α-chymotrypsin and, trypsin.

15. The depilatory composition of claim 10 wherein the second component further comprises an effective amount 0.001M hydrochloric acid.

16. The depilatory composition of claim 10 wherein the amount of the proteolytic enzyme in the second component is sufficient to provide a concentration of the proteolytic enzyme in the second component of about 3.4 mg/ml and a concentration of the proteolytic enzyme in the composition of about 0.05 mg/ml.

17. The depilatory composition of claim 10 wherein the proteolytic enzyme is α-chymotrypsin and the pH of the combination of the first and second components is 7.5 to 8.0.

18. The depilatory composition of claim 10 herein the proteolytic enzyme is trypsin and the pH of the combination of the first and second components is 8.5 to 9.0.

19. A method of removing hair from the skin of a warm blooded animal comprising treating the skin of the warm blooded animal with an effective amount of the depilatory composition of claim 10.

20. A method of removing hair from the skin of a warm blooded animal comprising:
   a) treating the skin of the warm blooded animal with an effective amount of the depilatory composition of claim 12; and
   b) treating the skin of the warm blooded animal with an effective amount of the depilatory composition of claim 18.

* * * * *